US010857233B1

(12) United States Patent
Bermudes

(10) Patent No.: US 10,857,233 B1
(45) Date of Patent: Dec. 8, 2020

(54) PROTEASE INHIBITOR COMBINATION WITH THERAPEUTIC PROTEINS INCLUDING ANTIBODIES

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 495 days.

(21) Appl. No.: 15/463,676

(22) Filed: Mar. 20, 2017

Related U.S. Application Data

(62) Division of application No. 13/024,179, filed on Feb. 9, 2011, now Pat. No. 9,597,379.

(60) Provisional application No. 61/302,763, filed on Feb. 9, 2010.

(51) Int. Cl.
| | |
|---|---|
| *A61K 38/55* | (2006.01) |
| *A61K 38/43* | (2006.01) |
| *A61K 38/10* | (2006.01) |
| *A61K 39/395* | (2006.01) |
| *C07K 16/28* | (2006.01) |
| *C07K 16/46* | (2006.01) |
| *A61K 47/48* | (2006.01) |

(52) U.S. Cl.
CPC ........ *A61K 47/48561* (2013.01); *A61K 38/10* (2013.01); *A61K 38/43* (2013.01); *A61K 38/55* (2013.01); *A61K 39/3955* (2013.01); *A61K 47/48246* (2013.01); *C07K 16/2863* (2013.01); *C07K 16/46* (2013.01); *C07K 2317/24* (2013.01); *C07K 2319/30* (2013.01); *C07K 2319/50* (2013.01)

(58) Field of Classification Search
None
See application file for complete search history.

(56) References Cited

U.S. PATENT DOCUMENTS

| | | |
|---|---|---|
| 4,436,727 A | 3/1984 | Ribi |
| 4,906,567 A | 3/1990 | Connelly |
| 5,021,234 A | 6/1991 | Ehrenfeld |
| 5,087,569 A | 2/1992 | Gabay et al. |
| 5,126,257 A | 6/1992 | Gabay et al. |
| 5,143,830 A | 9/1992 | Holland et al. |
| 5,223,409 A | 6/1993 | Ladner et al. |
| 5,250,515 A | 10/1993 | Fuchs et al. |
| 5,278,049 A | 1/1994 | Baker et al. |
| 5,281,530 A | 1/1994 | Sick et al. |
| 5,318,900 A | 6/1994 | Habuka et al. |
| 5,338,724 A | 8/1994 | Gabay et al. |
| 5,344,762 A | 9/1994 | Karapetian |
| 5,354,675 A | 10/1994 | Iida et al. |
| 5,399,490 A | 3/1995 | Balganesh et al. |
| 5,403,484 A | 4/1995 | Ladner et al. |
| 5,466,463 A | 11/1995 | Ford |
| 5,466,672 A | 11/1995 | Kushnaryov et al. |
| 5,495,001 A | 2/1996 | McGrogan et al. |
| 5,506,139 A | 4/1996 | Loosmore et al. |
| 5,569,597 A | 10/1996 | Grimsley et al. |
| 5,571,698 A | 11/1996 | Ladner et al. |
| 5,604,201 A | 2/1997 | Thomas et al. |
| 5,635,484 A | 6/1997 | Ayres et al. |
| 5,651,965 A | 7/1997 | Payne |
| 5,656,436 A | 8/1997 | Loosmore et al. |
| 5,665,353 A | 9/1997 | Loosmore et al. |
| 5,705,151 A | 1/1998 | Dow et al. |
| 5,712,369 A | 1/1998 | Old et al. |
| 5,824,538 A | 10/1998 | Branstrom et al. |
| 5,830,702 A | 11/1998 | Portnoy et al. |
| 5,837,500 A | 11/1998 | Ladner et al. |
| 5,869,302 A | 2/1999 | Loosmore et al. |
| 5,877,159 A | 3/1999 | Powell et al. |
| 5,935,573 A | 8/1999 | Loosmore et al. |
| 5,939,297 A | 8/1999 | Loosmore et al. |

(Continued)

FOREIGN PATENT DOCUMENTS

| | | |
|---|---|---|
| WO | WO9100014 | 1/1991 |
| WO | WO1991000014 | 1/1991 |
| WO | WO9106317 | 5/1991 |
| WO | WO9211361 | 7/1992 |
| WO | WO9215689 | 9/1992 |
| WO | WO9502048 | 1/1995 |
| WO | WO9505835 | 3/1995 |
| WO | WO9509655 | 4/1995 |
| WO | WO9611277 | 4/1996 |
| WO | WO9634631 | 11/1996 |
| WO | WO9638159 | 12/1996 |
| WO | WO9640238 | 12/1996 |

(Continued)

OTHER PUBLICATIONS

Rawlings, N.D., et al. 2004 Biochem J 378: 705-716. (Year: 2004).*
Huang, Xin, Yahui Yan, Yizheng Tu, Jeffrey Gatti, George J. Broze Jr, Aiwu Zhou, and Steven T. Olson. "Structural basis for catalytic activation of protein Z-dependent protease inhibitor (ZPI) by protein Z." Blood, The Journal of the American Society of Hematology 120, No. 8 (2012): 1726-1733.

*Primary Examiner* — Marsha Tsay
(74) *Attorney, Agent, or Firm* — Hoffberg & Associates; Steven M. Hoffberg

(57) ABSTRACT

Protease inhibitors together with protease sensitive therapeutics or diagnostics are provided, which may be ionically or covalently bound, or unbound. The protease inhibitors and/or protease sensitive moiety may be provided in monomeric, homopolymeric, heteropolymeric (for each of the protease and agent) and/or block copolymeric (combining polymers of agent and inhibitor) form. The inhibitors may be native active or e.g., protease activated. Multiple protease inhibitor peptides may be used in-frame with multiple protease cleavage signals (polymeric protease activated protease inhibitors). Combination with the protease inhibitors with the protease sensitive therapeutic enhances the intact, active molecule local-regional or targeted cell or tissue concentration, peak concentration and/or duration of the therapeutic exposure, thereby increasing its therapeutic efficacy. The protease inhibitors are particularly useful for tumor-targeted therapies and for vaccines.

18 Claims, 1 Drawing Sheet
Specification includes a Sequence Listing.

(56) References Cited

U.S. PATENT DOCUMENTS

| | | |
|---|---|---|
| 5,945,102 A | 8/1999 | de Faire et al. |
| 5,958,406 A | 9/1999 | de Faire et al. |
| 5,962,430 A | 10/1999 | Loosmore et al. |
| 5,981,503 A | 11/1999 | Loosmore et al. |
| 5,997,881 A | 12/1999 | Powell et al. |
| 6,004,562 A | 12/1999 | Campagnari |
| 6,020,183 A | 2/2000 | Loosmore et al. |
| 6,022,855 A | 2/2000 | Thomas et al. |
| 6,025,342 A | 2/2000 | Loosmore et al. |
| 6,030,612 A | 2/2000 | de Faire et al. |
| 6,030,780 A | 2/2000 | Vinkemeier et al. |
| 6,037,526 A | 3/2000 | Grimsley et al. |
| 6,051,237 A | 4/2000 | Paterson |
| 6,080,849 A | 6/2000 | Bermudes et al. |
| 6,114,125 A | 9/2000 | Loosmore et al. |
| 6,143,551 A | 11/2000 | Goebel |
| 6,147,057 A | 11/2000 | Loosmore et al. |
| 6,150,170 A | 11/2000 | Powell et al. |
| 6,153,580 A | 11/2000 | Loosmore et al. |
| 6,177,083 B1 | 1/2001 | Lubitz |
| 6,190,657 B1 | 2/2001 | Pawelek et al. |
| 6,207,156 B1 | 3/2001 | Kuchroo et al. |
| 6,232,110 B1 | 5/2001 | Pallas et al. |
| 6,245,892 B1 | 6/2001 | Oaks et al. |
| 6,251,406 B1 | 6/2001 | Haefliger et al. |
| 6,277,379 B1 | 8/2001 | Oaks et al. |
| 6,329,002 B1 | 12/2001 | Kim et al. |
| 6,348,344 B1 | 2/2002 | Ayal-Hershkovitz et al. |
| 6,355,790 B1 | 3/2002 | Rosenblatt et al. |
| 6,376,234 B1 | 4/2002 | Grimsley et al. |
| 6,410,012 B1 | 6/2002 | Sizemore et al. |
| 6,447,777 B1 | 9/2002 | Terman et al. |
| 6,447,784 B1 | 9/2002 | Bermudes et al. |
| 6,475,482 B1 | 11/2002 | Bermudes et al. |
| 6,475,763 B1 | 11/2002 | Ayal-Hershkovitz et al. |
| 6,537,558 B2 | 3/2003 | Kaniga |
| 6,548,287 B1 | 4/2003 | Powell et al. |
| 6,605,286 B2 | 8/2003 | Steidler et al. |
| 6,605,697 B1 | 8/2003 | Kwon et al. |
| 6,638,912 B2 | 10/2003 | Bhatnagar et al. |
| 6,680,374 B2 | 1/2004 | Oaks et al. |
| 6,685,935 B1 | 2/2004 | Pawelek et al. |
| 6,743,893 B2 | 6/2004 | Engler et al. |
| 6,746,671 B2 | 6/2004 | Steidler et al. |
| 6,841,535 B2 | 1/2005 | Divita et al. |
| 6,863,894 B2 | 3/2005 | Bermudes et al. |
| 6,923,972 B2 | 8/2005 | Bermudes et al. |
| 6,962,696 B1 | 11/2005 | Bermudes et al. |
| 6,979,538 B2 | 12/2005 | Ladner et al. |
| 7,001,884 B2 | 2/2006 | Komiyama et al. |
| 7,033,991 B2 | 4/2006 | Lindberg et al. |
| 7,118,879 B2 | 10/2006 | Ladner et al. |
| 7,208,293 B2 | 4/2007 | Ladner et al. |
| 7,258,863 B2 | 8/2007 | Oaks et al. |
| 7,354,592 B2 | 4/2008 | Bermudes et al. |
| 7,358,084 B2 | 4/2008 | Kolkman |
| 7,390,646 B2 | 6/2008 | Andino-Pavlovsky et al. |
| 7,413,877 B2 | 8/2008 | Collier et al. |
| 7,452,531 B2 | 11/2008 | Bermudes et al. |
| 7,514,089 B2 | 4/2009 | Bermudes et al. |
| 7,569,547 B2 | 8/2009 | Lindberg et al. |
| 7,635,682 B2 | 12/2009 | Denmeade et al. |
| 7,666,627 B2 | 2/2010 | Gal et al. |
| 7,691,599 B2 | 4/2010 | Rubin |
| 7,696,173 B2 | 4/2010 | Collier et al. |
| 7,700,349 B2 | 4/2010 | Romaine et al. |
| 7,700,830 B2 | 4/2010 | Corbin et al. |
| 7,705,195 B2 | 4/2010 | French et al. |
| 7,718,618 B2 | 5/2010 | Gallo et al. |
| 7,776,823 B2 | 8/2010 | Gallo et al. |
| 7,803,918 B2 | 9/2010 | van der Hoek |
| 7,846,678 B2 | 12/2010 | Pepe et al. |
| 7,850,970 B2 | 12/2010 | Shapiro |
| 7,887,794 B2 | 2/2011 | Luquet et al. |
| 7,888,321 B2 | 2/2011 | Cooper et al. |
| 7,892,803 B2 | 2/2011 | Tanner et al. |
| 7,892,825 B2 | 2/2011 | Barr et al. |
| 7,893,007 B2 | 2/2011 | Ladner et al. |
| 7,943,754 B2 | 5/2011 | Bentwich et al. |
| 7,947,822 B2 | 5/2011 | Nabel et al. |
| 7,964,362 B2 | 6/2011 | Lee et al. |
| 7,989,202 B1 | 8/2011 | Mach et al. |
| 8,030,447 B2 | 10/2011 | Motin et al. |
| 8,030,542 B2 | 10/2011 | Corbin et al. |
| 8,062,885 B2 | 11/2011 | Mach et al. |
| 8,101,349 B2 | 1/2012 | Garcia et al. |
| 8,101,826 B2 | 1/2012 | Romano |
| 8,119,354 B2 | 2/2012 | Katanaev |
| 8,128,922 B2 | 3/2012 | Wu et al. |
| 8,153,414 B2 | 4/2012 | Caplan et al. |
| 8,173,397 B2 | 5/2012 | Gal et al. |
| 8,206,700 B2 | 6/2012 | Horwitz et al. |
| 8,231,878 B2 | 7/2012 | Colonna et al. |
| 8,236,315 B2 | 8/2012 | Lazarides et al. |
| 8,241,623 B1 | 8/2012 | Bermudes |
| 8,244,484 B2 | 8/2012 | Lee et al. |
| 8,246,945 B2 | 8/2012 | Caplan et al. |
| 8,283,319 B2 | 10/2012 | Schulte et al. |
| 8,323,961 B2 | 12/2012 | Nabel et al. |
| 8,349,570 B2 | 1/2013 | Pepe et al. |
| 8,372,620 B2 | 2/2013 | Sibbesen et al. |
| 8,440,207 B2 | 5/2013 | Bermudes |
| 8,445,650 B2 | 5/2013 | Simpson et al. |
| 8,507,249 B2 | 8/2013 | Finlay et al. |
| 8,524,220 B1 | 9/2013 | Bermudes |
| 8,603,824 B2 | 12/2013 | Ramseier et al. |
| 8,609,358 B2 | 12/2013 | Sebastian et al. |
| 8,623,350 B1 | 1/2014 | Bermudes |
| 8,628,782 B2 | 1/2014 | Berkower |
| 8,633,305 B2 | 1/2014 | Shapiro |
| 8,647,642 B2 | 2/2014 | Bermudes |
| 8,685,392 B2 | 4/2014 | Helmerhorst et al. |
| 8,686,218 B2 | 4/2014 | Romaine et al. |
| 8,722,584 B2 | 5/2014 | Delisa et al. |
| 8,741,313 B2 | 6/2014 | Sable et al. |
| 8,748,373 B2 | 6/2014 | Chai et al. |
| 8,758,771 B2 | 6/2014 | Finlay et al. |
| 8,759,086 B2 | 6/2014 | Mach et al. |
| 8,771,669 B1 | 7/2014 | Bermudes |
| 8,771,671 B2 | 7/2014 | Spencer et al. |
| 8,791,237 B2 | 7/2014 | Paterson et al. |
| 8,795,730 B2 | 8/2014 | Vachon |
| 8,815,251 B2 | 8/2014 | Caplan et al. |
| 8,821,893 B2 | 9/2014 | Dattwyler et al. |
| 8,835,107 B2 | 9/2014 | Van Der Hoek |
| 8,853,362 B2 | 10/2014 | Tissot et al. |
| 8,906,662 B2 | 12/2014 | Nataro et al. |
| 8,920,809 B2 | 12/2014 | Dirienzo |
| 8,926,993 B2 | 1/2015 | Dubensky, Jr. et al. |
| 8,951,992 B2 | 2/2015 | Nathan et al. |
| 8,956,859 B1 | 2/2015 | Bermudes |
| 8,962,816 B2 | 2/2015 | Ertl et al. |
| 8,969,542 B2 | 3/2015 | Buyse et al. |
| 8,981,061 B2 | 3/2015 | Colonna et al. |
| 8,999,949 B2 | 4/2015 | Spencer et al. |
| 9,068,187 B1 | 6/2015 | Bermudes |
| 9,109,229 B2 | 8/2015 | Ramseier et al. |
| 9,161,974 B2 | 10/2015 | Dubensky et al. |
| 9,187,523 B2 | 11/2015 | Motin et al. |
| 9,187,762 B2 | 11/2015 | Albert et al. |
| 9,198,960 B2 | 12/2015 | Dubensky, Jr. et al. |
| 9,200,251 B1 | 12/2015 | Bermudes |
| 9,200,289 B1 | 12/2015 | Bermudes |
| 9,206,456 B2 | 12/2015 | Lenormand |
| 9,315,817 B2 | 4/2016 | Bermudes |
| 9,365,625 B1 | 6/2016 | Bermudes |
| 9,421,252 B2 | 8/2016 | Bermudes |
| 9,486,513 B1 | 11/2016 | Bermudes |
| 9,593,339 B1 | 3/2017 | Bermudes |
| 9,597,379 B1 | 3/2017 | Bermudes |
| 9,616,114 B1 | 4/2017 | Bermudes |
| 9,657,085 B1 | 5/2017 | Bermudes |
| 9,737,592 B1 | 8/2017 | Bermudes et al. |
| 9,739,773 B1 | 8/2017 | Bermudes |

(56) References Cited

U.S. PATENT DOCUMENTS

| | | |
|---|---|---|
| 9,878,023 B1 | 1/2018 | Bermudes |
| 2001/0006642 A1 | 7/2001 | Steidler et al. |
| 2001/0009957 A1 | 7/2001 | Oaks et al. |
| 2001/0029024 A1 | 10/2001 | Kodadek |
| 2001/0029043 A1 | 10/2001 | Haefliger et al. |
| 2002/0016982 A1 | 2/2002 | Romaine et al. |
| 2002/0026655 A1 | 2/2002 | Bermudes et al. |
| 2002/0106380 A1 | 8/2002 | Hung et al. |
| 2002/0107374 A1 | 8/2002 | Pallas et al. |
| 2002/0123053 A1 | 9/2002 | Luo et al. |
| 2002/0150881 A1 | 10/2002 | Ladner et al. |
| 2002/0197276 A1 | 12/2002 | Oaks et al. |
| 2003/0059400 A1 | 3/2003 | Szalay |
| 2003/0082219 A1 | 5/2003 | Warren et al. |
| 2003/0087827 A1 | 5/2003 | Lindberg et al. |
| 2003/0092066 A1 | 5/2003 | Vinkemeier et al. |
| 2003/0106096 A1 | 6/2003 | Barry |
| 2003/0109026 A1 | 6/2003 | Bermudes et al. |
| 2003/0113293 A1 | 6/2003 | Bermudes et al. |
| 2003/0113717 A1 | 6/2003 | Ladner et al. |
| 2003/0115630 A1 | 6/2003 | Romano |
| 2003/0124561 A1 | 7/2003 | Mach et al. |
| 2003/0131372 A1 | 7/2003 | Copenhaver et al. |
| 2003/0131376 A1 | 7/2003 | Okubara et al. |
| 2003/0144490 A1 | 7/2003 | Edwards et al. |
| 2003/0165875 A1 | 9/2003 | Colonna et al. |
| 2003/0166140 A1 | 9/2003 | Chen et al. |
| 2003/0170276 A1 | 9/2003 | Bermudes et al. |
| 2003/0186416 A1 | 10/2003 | Pallas et al. |
| 2003/0188336 A1 | 10/2003 | Corbin et al. |
| 2003/0203377 A1 | 10/2003 | Milne Edwards et al. |
| 2003/0211476 A1 | 11/2003 | O'Mahony et al. |
| 2003/0219722 A1 | 11/2003 | Ladner et al. |
| 2003/0219886 A1 | 11/2003 | Ladner et al. |
| 2004/0005539 A1 | 1/2004 | Ladner et al. |
| 2004/0013658 A1 | 1/2004 | Fulton et al. |
| 2004/0023205 A1 | 2/2004 | Ladner et al. |
| 2004/0023282 A1 | 2/2004 | Luo et al. |
| 2004/0038307 A1 | 2/2004 | Lee et al. |
| 2004/0096426 A1 | 5/2004 | Chen et al. |
| 2004/0101531 A1 | 5/2004 | Curtiss et al. |
| 2004/0110939 A1 | 6/2004 | Dumas Milne Edwards et al. |
| 2004/0115788 A1 | 6/2004 | Zheng et al. |
| 2004/0133930 A1 | 7/2004 | Cooper et al. |
| 2004/0180380 A1 | 9/2004 | Lee et al. |
| 2004/0191787 A1 | 9/2004 | Tanner et al. |
| 2004/0219169 A1 | 11/2004 | Bermudes et al. |
| 2004/0229338 A1 | 11/2004 | King |
| 2004/0234956 A1 | 11/2004 | Kabat et al. |
| 2004/0234998 A1 | 11/2004 | Sibbesen et al. |
| 2004/0266674 A1 | 12/2004 | Mills et al. |
| 2005/0013822 A1 | 1/2005 | Oaks et al. |
| 2005/0032157 A1 | 2/2005 | Gal et al. |
| 2005/0036987 A1 | 2/2005 | Pawelek et al. |
| 2005/0055746 A1 | 3/2005 | Michaud et al. |
| 2005/0063994 A1 | 3/2005 | Caplan et al. |
| 2005/0069532 A1 | 3/2005 | Weinrauch et al. |
| 2005/0069911 A1 | 3/2005 | Lee et al. |
| 2005/0070007 A1 | 3/2005 | Romaine et al. |
| 2005/0074463 A1 | 4/2005 | Autran et al. |
| 2005/0079573 A1 | 4/2005 | Sibbesen |
| 2005/0084972 A1 | 4/2005 | Barr et al. |
| 2005/0106151 A1 | 5/2005 | Shapiro |
| 2005/0112139 A1 | 5/2005 | Karp |
| 2005/0118193 A1 | 6/2005 | Andino-Pavlovsky et al. |
| 2005/0148504 A1 | 7/2005 | Katunuma et al. |
| 2005/0158295 A1 | 7/2005 | Swiercz et al. |
| 2005/0166274 A1 | 7/2005 | French et al. |
| 2005/0180963 A1 | 8/2005 | Adams et al. |
| 2005/0202535 A1 | 9/2005 | Collier et al. |
| 2005/0203007 A1 | 9/2005 | Komiyama et al. |
| 2005/0208033 A1 | 9/2005 | Luquet et al. |
| 2005/0227917 A1 | 10/2005 | Williams et al. |
| 2005/0241015 A1 | 10/2005 | Mach et al. |
| 2005/0241016 A1 | 10/2005 | Mach et al. |
| 2005/0249706 A1 | 11/2005 | Bermudes et al. |
| 2005/0251885 A1 | 11/2005 | Michaud et al. |
| 2005/0255088 A1 | 11/2005 | Bermudes et al. |
| 2005/0257282 A1 | 11/2005 | Mach et al. |
| 2005/0260670 A1 | 11/2005 | Colonna et al. |
| 2005/0266560 A1 | 12/2005 | Preuss et al. |
| 2005/0268359 A1 | 12/2005 | Mach et al. |
| 2005/0273882 A1 | 12/2005 | Romano |
| 2005/0281828 A1 | 12/2005 | Bowdish et al. |
| 2006/0009633 A9 | 1/2006 | Dumas Milne Edwards et al. |
| 2006/0014212 A1 | 1/2006 | Benkovic et al. |
| 2006/0024668 A1 | 2/2006 | Hoek |
| 2006/0035270 A1 | 2/2006 | Lee et al. |
| 2006/0035320 A1 | 2/2006 | Tissot et al. |
| 2006/0035371 A1 | 2/2006 | Zheng et al. |
| 2006/0084113 A1 | 4/2006 | Ladner et al. |
| 2006/0088910 A1 | 4/2006 | Nguyen |
| 2006/0110747 A1 | 5/2006 | Ramseier et al. |
| 2006/0156440 A1 | 7/2006 | Michaud et al. |
| 2006/0160152 A1 | 7/2006 | Vinkemeier et al. |
| 2006/0174357 A1 | 8/2006 | Velander et al. |
| 2006/0182762 A1 | 8/2006 | Maas et al. |
| 2006/0223142 A1 | 10/2006 | Dumas Milne Edwards et al. |
| 2006/0229336 A1 | 10/2006 | Kazmierski et al. |
| 2006/0241050 A1 | 10/2006 | Cameron et al. |
| 2006/0269561 A1 | 11/2006 | Paterson et al. |
| 2006/0275823 A1 | 12/2006 | Kodadek |
| 2006/0275897 A1 | 12/2006 | Nabel et al. |
| 2006/0286639 A1 | 12/2006 | Dumas Milne Edwards et al. |
| 2007/0009489 A1 | 1/2007 | Bermudes et al. |
| 2007/0020327 A1 | 1/2007 | Fikes et al. |
| 2007/0028324 A1 | 2/2007 | Corbin et al. |
| 2007/0037744 A1 | 2/2007 | Gallo et al. |
| 2007/0041997 A1 | 2/2007 | Finlay et al. |
| 2007/0059799 A1 | 3/2007 | Sette et al. |
| 2007/0065908 A1 | 3/2007 | Gallo et al. |
| 2007/0071773 A1 | 3/2007 | Hanski et al. |
| 2007/0143871 A1 | 6/2007 | French et al. |
| 2007/0192905 A1 | 8/2007 | Piller et al. |
| 2007/0254329 A1 | 11/2007 | Rubin |
| 2007/0259417 A1 | 11/2007 | Ladner et al. |
| 2007/0275423 A1 | 11/2007 | Sebastian et al. |
| 2007/0298012 A1 | 12/2007 | King et al. |
| 2008/0019994 A1 | 1/2008 | Brunham et al. |
| 2008/0038296 A1 | 2/2008 | Brahmbhatt et al. |
| 2008/0070255 A1 | 3/2008 | Tanner et al. |
| 2008/0089862 A1 | 4/2008 | Benhar et al. |
| 2008/0090770 A1 | 4/2008 | Belmares et al. |
| 2008/0124355 A1 | 5/2008 | Bermudes |
| 2008/0181892 A1 | 7/2008 | Ledbetter et al. |
| 2008/0255025 A1* | 10/2008 | Ladner ............... C07K 14/8114 514/1.1 |
| 2008/0261869 A1 | 10/2008 | Shapiro |
| 2008/0269070 A1 | 10/2008 | Ramseier et al. |
| 2008/0286290 A1 | 11/2008 | Furusako et al. |
| 2008/0286306 A1 | 11/2008 | Nabel et al. |
| 2008/0288264 A1 | 11/2008 | Mach et al. |
| 2008/0311081 A1 | 12/2008 | Fruehauf et al. |
| 2009/0011974 A1 | 1/2009 | Bocharov et al. |
| 2009/0019609 A1 | 1/2009 | Romano |
| 2009/0023157 A1 | 1/2009 | Lee et al. |
| 2009/0042248 A1 | 2/2009 | Gal et al. |
| 2009/0042278 A1 | 2/2009 | Barr et al. |
| 2009/0069248 A1 | 3/2009 | Motin et al. |
| 2009/0081199 A1 | 3/2009 | Colonna et al. |
| 2009/0111160 A1 | 4/2009 | Collier et al. |
| 2009/0123426 A1 | 5/2009 | Li et al. |
| 2009/0162356 A1 | 6/2009 | Lookeren Campagne |
| 2009/0169517 A1 | 7/2009 | Bermudes et al. |
| 2009/0169566 A1 | 7/2009 | Rawlin et al. |
| 2009/0209749 A1 | 8/2009 | Mach et al. |
| 2009/0214506 A1 | 8/2009 | Hardy et al. |
| 2009/0217396 A1 | 8/2009 | Kyrkanides et al. |
| 2009/0232804 A1 | 9/2009 | Lazarides et al. |
| 2009/0234101 A1 | 9/2009 | Ladner et al. |
| 2009/0239797 A1 | 9/2009 | Cooper et al. |
| 2009/0240073 A1 | 9/2009 | Barry |
| 2009/0246220 A1 | 10/2009 | Ertl et al. |
| 2009/0258935 A1 | 10/2009 | Zheng et al. |

(56) References Cited

U.S. PATENT DOCUMENTS

| | | |
|---|---|---|
| 2009/0294288 A1 | 12/2009 | May et al. |
| 2009/0297560 A1 | 12/2009 | Dattwyler et al. |
| 2009/0305296 A1 | 12/2009 | Bengtsson et al. |
| 2009/0317418 A1 | 12/2009 | Catanzaro et al. |
| 2010/0022584 A1 | 1/2010 | Kenyon et al. |
| 2010/0086546 A1 | 4/2010 | Lee et al. |
| 2010/0111998 A1 | 5/2010 | Nabel et al. |
| 2010/0135961 A1 | 6/2010 | Bermudes |
| 2010/0136048 A1 | 6/2010 | Bermudes |
| 2010/0137162 A1 | 6/2010 | Retallack et al. |
| 2010/0137192 A1 | 6/2010 | Shapiro |
| 2010/0166802 A1 | 7/2010 | Caplan et al. |
| 2010/0169988 A1 | 7/2010 | Kohli et al. |
| 2010/0184613 A1 | 7/2010 | Lee et al. |
| 2010/0189774 A1 | 7/2010 | Lenormand |
| 2010/0215679 A1 | 8/2010 | Horwitz et al. |
| 2010/0215682 A1 | 8/2010 | Berkower |
| 2010/0239546 A1 | 9/2010 | Fruehauf et al. |
| 2010/0247544 A1 | 9/2010 | Vachon |
| 2010/0247560 A1 | 9/2010 | Simpson et al. |
| 2010/0261201 A1 | 10/2010 | Katanaev |
| 2010/0272750 A1 | 10/2010 | Buyse et al. |
| 2010/0278819 A1 | 11/2010 | Bossuyt et al. |
| 2010/0279923 A1 | 11/2010 | Schulte et al. |
| 2010/0286251 A1 | 11/2010 | Rubin |
| 2010/0305306 A1 | 12/2010 | Colonna et al. |
| 2010/0310560 A1 | 12/2010 | Colonna et al. |
| 2010/0319087 A1 | 12/2010 | Corbin et al. |
| 2010/0333235 A1 | 12/2010 | Mach et al. |
| 2011/0014701 A1 | 1/2011 | Ghosh |
| 2011/0021416 A1 | 1/2011 | Shapiro |
| 2011/0027349 A1 | 2/2011 | Sable et al. |
| 2011/0028397 A1 | 2/2011 | Tozser et al. |
| 2011/0038917 A1 | 2/2011 | Kappers et al. |
| 2011/0065091 A1 | 3/2011 | Van Der Hoek |
| 2011/0104146 A1 | 5/2011 | Faraday |
| 2011/0111496 A1 | 5/2011 | Li |
| 2011/0152176 A1 | 6/2011 | Horswill |
| 2011/0189774 A1 | 8/2011 | Mach et al. |
| 2011/0190234 A1 | 8/2011 | Nathan et al. |
| 2011/0195423 A1 | 8/2011 | Selinfreund et al. |
| 2011/0201109 A1 | 8/2011 | Zwaka et al. |
| 2011/0223241 A1 | 9/2011 | Tardi et al. |
| 2011/0257080 A1 | 10/2011 | Chai et al. |
| 2011/0262474 A1 | 10/2011 | Du et al. |
| 2011/0274721 A1 | 11/2011 | Nabel et al. |
| 2011/0275585 A1 | 11/2011 | Brahmbhatt et al. |
| 2011/0277180 A1 | 11/2011 | Romano |
| 2011/0287037 A1 | 11/2011 | Gentschev et al. |
| 2011/0293608 A1 | 12/2011 | Jaffee et al. |
| 2011/0305724 A1 | 12/2011 | Paterson et al. |
| 2012/0027785 A1 | 2/2012 | Dirienzo |
| 2012/0042413 A1 | 2/2012 | Albert et al. |
| 2012/0045474 A1 | 2/2012 | Motin et al. |
| 2012/0064062 A1 | 3/2012 | Goguen et al. |
| 2012/0064572 A1 | 3/2012 | Finlay et al. |
| 2012/0071545 A1 | 3/2012 | Shapiro |
| 2012/0088314 A1 | 4/2012 | Katanaev |
| 2012/0093773 A1 | 4/2012 | Li et al. |
| 2012/0142080 A1 | 6/2012 | Bermudes |
| 2012/0142623 A1 | 6/2012 | Lagunoff et al. |
| 2012/0164687 A1 | 6/2012 | Bereta et al. |
| 2012/0219545 A1 | 8/2012 | Ayuso et al. |
| 2012/0230976 A1 | 9/2012 | Helmerhorst et al. |
| 2012/0271036 A1 | 10/2012 | Smith et al. |
| 2012/0276132 A1 | 11/2012 | Feng et al. |
| 2012/0308575 A1 | 12/2012 | Guo et al. |
| 2013/0017173 A1 | 1/2013 | Nataro et al. |
| 2013/0023472 A1 | 1/2013 | Bristow |
| 2013/0028901 A1 | 1/2013 | Colonna et al. |
| 2013/0028924 A1 | 1/2013 | Ertl et al. |
| 2013/0102017 A1 | 4/2013 | Pfaendler et al. |
| 2013/0122043 A1 | 5/2013 | Guimaraes et al. |
| 2013/0129713 A1 | 5/2013 | Rescigno et al. |
| 2013/0150559 A1 | 6/2013 | Colonna et al. |
| 2013/0171109 A1 | 7/2013 | Helmerhorst et al. |
| 2013/0196432 A1 | 8/2013 | Poehlmann et al. |
| 2013/0202557 A1 | 8/2013 | Li et al. |
| 2013/0209405 A1 | 8/2013 | Curtiss et al. |
| 2013/0269057 A1 | 10/2013 | Fosu-Nyarko et al. |
| 2013/0276168 A1 | 10/2013 | Romaine et al. |
| 2013/0344033 A1 | 12/2013 | Vergnolle et al. |
| 2014/0005108 A1 | 1/2014 | Bristow |
| 2014/0056841 A1 | 2/2014 | Vachon |
| 2014/0057940 A1 | 2/2014 | Mankowski et al. |
| 2014/0093528 A1 | 4/2014 | Berkower |
| 2014/0150134 A1 | 5/2014 | Li et al. |
| 2014/0155343 A1 | 6/2014 | Brahmbhatt et al. |
| 2014/0162279 A1 | 6/2014 | Ramseier et al. |
| 2014/0162952 A1 | 6/2014 | Katagiri et al. |
| 2014/0173774 A1 | 6/2014 | Pareddy et al. |
| 2014/0173780 A1 | 6/2014 | Pareddy et al. |
| 2014/0194346 A1 | 7/2014 | Aebi et al. |
| 2014/0220661 A1 | 8/2014 | Bermudes |
| 2014/0227286 A1 | 8/2014 | Jaffee et al. |
| 2014/0234310 A1 | 8/2014 | Shapiro |
| 2014/0287419 A1 | 9/2014 | Althoff et al. |
| 2014/0289906 A1 | 9/2014 | Althoff et al. |
| 2014/0296480 A1 | 10/2014 | Sanchez Garcia et al. |
| 2014/0322790 A1 | 10/2014 | Sebastian et al. |
| 2014/0370036 A1 | 12/2014 | Shapiro |
| 2015/0004705 A1 | 1/2015 | Lu et al. |
| 2015/0017138 A1 | 1/2015 | Fruehauf et al. |
| 2015/0017204 A1 | 1/2015 | Bermudes |
| 2015/0030573 A1 | 1/2015 | Fruehauf et al. |
| 2015/0044256 A1 | 2/2015 | Dattwyler et al. |
| 2015/0050308 A1 | 2/2015 | van der Hoek |
| 2015/0057191 A1 | 2/2015 | Tissot et al. |
| 2015/0071957 A1 | 3/2015 | Kelly et al. |
| 2015/0125849 A1 | 5/2015 | Yeh et al. |
| 2015/0132330 A1 | 5/2015 | Garcia-Sastre et al. |
| 2015/0139940 A1 | 5/2015 | Bermudez Humaran et al. |
| 2015/0153358 A1 | 6/2015 | Ayuso et al. |
| 2015/0184220 A1 | 7/2015 | Sebastian et al. |
| 2015/0197748 A1 | 7/2015 | Liu et al. |
| 2015/0216965 A1 | 8/2015 | Diamond et al. |
| 2015/0225692 A1 | 8/2015 | Bhatia et al. |
| 2015/0231207 A1 | 8/2015 | Kaspar |
| 2015/0246137 A1 | 9/2015 | Guo et al. |
| 2015/0291667 A1 | 10/2015 | Dirienzo |
| 2015/0337321 A1 | 11/2015 | Mach et al. |
| 2015/0351390 A1 | 12/2015 | Castle et al. |
| 2015/0355172 A1 | 12/2015 | Kraus et al. |

FOREIGN PATENT DOCUMENTS

| | | |
|---|---|---|
| WO | WO1996040238 | 12/1996 |
| WO | WO9708955 | 3/1997 |
| WO | WO9714782 | 4/1997 |
| WO | WO1997014782 | 4/1997 |
| WO | WO9718225 | 5/1997 |
| WO | WO9718837 | 5/1997 |
| WO | WO9719688 | 6/1997 |
| WO | WO9725061 | 7/1997 |
| WO | WO9833923 | 8/1998 |
| WO | WO9910014 | 3/1999 |
| WO | WO9910485 | 3/1999 |
| WO | WO9913003 | 3/1999 |
| WO | WO9913053 | 3/1999 |
| WO | WO1999010014 | 3/1999 |
| WO | WO1999010485 | 3/1999 |
| WO | WO9952563 | 10/1999 |
| WO | WO0004919 | 2/2000 |
| WO | WO0009733 | 2/2000 |
| WO | WO2000004919 | 2/2000 |
| WO | WO0114579 | 3/2001 |
| WO | WO2001014579 | 3/2001 |
| WO | WO0125397 | 4/2001 |
| WO | WO2001025397 | 4/2001 |
| WO | WO0220809 | 3/2002 |
| WO | WO02070645 | 9/2002 |
| WO | WO2002070645 | 9/2002 |
| WO | WO03072125 | 9/2003 |
| WO | WO2003072125 | 9/2003 |

(56) References Cited

FOREIGN PATENT DOCUMENTS

| | | |
|---|---|---|
| WO | WO03102168 | 12/2003 |
| WO | WO2003102168 | 12/2003 |
| WO | WO2004076484 | 9/2004 |
| WO | WO2004103404 | 12/2004 |
| WO | WO2005014618 | 2/2005 |
| WO | WO2005018332 | 3/2005 |
| WO | WO2005054477 | 6/2005 |
| WO | WO2006010070 | 1/2006 |
| WO | WO2006013441 | 2/2006 |
| WO | WO2006048344 | 5/2006 |
| WO | WO2006116545 | 11/2006 |
| WO | WO2007083193 | 7/2007 |
| WO | WO2008073148 | 6/2008 |
| WO | WO2008091375 | 7/2008 |
| WO | WO2008156702 | 12/2008 |
| WO | WO2009006450 | 1/2009 |
| WO | WO2009006453 | 1/2009 |
| WO | WO2009014650 | 1/2009 |
| WO | WO2009086116 | 7/2009 |
| WO | WO2009126189 | 10/2009 |
| WO | WO2009139985 | 11/2009 |
| WO | WO2009145956 | 12/2009 |
| WO | WO2009150433 | 12/2009 |
| WO | WO2009152480 | 12/2009 |
| WO | WO2010036391 | 4/2010 |
| WO | WO2010057009 | 5/2010 |
| WO | WO2011017137 | 2/2011 |
| WO | WO2011086172 | 7/2011 |
| WO | WO2012104025 | 8/2012 |
| WO | WO2012150269 | 11/2012 |
| WO | WO8953854 | 5/2013 |
| WO | WO2013067185 | 5/2013 |

* cited by examiner

SEQUENCE LISTING

<160> NUMBER OF SEQ ID NOS: 47

<210> SEQ ID NO 1
<211> LENGTH: 58
<212> TYPE: PRT
<213> ORGANISM: Artificial Sequence
<220> FEATURE:
<223> OTHER INFORMATION: Aprotinin

<400> SEQUENCE: 1

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr
            20                  25                  30

Phe Val Tyr Gly Gly Cys Arg Ala Lys Arg Asn Asn Phe Lys Ser Ala
        35                  40                  45

Glu Asp Cys Met Arg Thr Cys Gly Gly Ala
    50                  55

<210> SEQ ID NO 2

```
<211> LENGTH: 14
<212> TYPE: PRT
<213> ORGANISM: Artificial Sequence
<220> FEATURE:
<223> OTHER INFORMATION: Protease Inhibitor 15 (amino acids 245-258 of
      human protease inhibitor)

<400> SEQUENCE: 2

Cys Phe Pro Gly Val Thr Ser Asn Tyr Leu Tyr Trp Phe Lys
1               5                   10

<210> SEQ ID NO 3
<211> LENGTH: 56
<212> TYPE: PRT
<213> ORGANISM: Artificial Sequence
<220> FEATURE:
<223> OTHER INFORMATION: Tissue Protease Inhibitor

<400> SEQUENCE: 3

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 4
<211> LENGTH: 36
<212> TYPE: PRT
<213> ORGANISM: Artificial Sequence
<220> FEATURE:
<223> OTHER INFORMATION: Furin Inhibitor

<400> SEQUENCE: 4

Pro Ala Ala Ala Thr Val Thr Lys Lys Val Ala Lys Ser Pro Lys Lys
1               5                   10                  15

Ala Lys Ala Ala Lys Pro Lys Lys Ala Ala Lys Ser Ala Ala Lys Ala
            20                  25                  30

Val Lys Pro Lys
        35

<210> SEQ ID NO 5
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 5

Thr Lys Lys Val Ala Lys Arg Pro Arg Ala Lys Arg Ala Ala
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 6

Thr Lys Lys Val Ala Lys Arg Pro Arg Ala Lys Arg Asp Leu
1               5                   10
```

```
<210> SEQ ID NO 7
<211> LENGTH: 9
<212> TYPE: PRT
<213> ORGANISM: Artificial Sequence
<220> FEATURE:
<223> OTHER INFORMATION: Furin Inhibitor

<400> SEQUENCE: 7

Gly Lys Arg Pro Arg Ala Lys Arg Ala
1               5

<210> SEQ ID NO 8
<211> LENGTH: 10
<212> TYPE: PRT
<213> ORGANISM: Artificial Sequence
<220> FEATURE:
<223> OTHER INFORMATION: Furin Inhibitor

<400> SEQUENCE: 8

Cys Lys Arg Pro Arg Ala Lys Arg Asp Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Furin Inhibitor

<400> SEQUENCE: 9

Cys Val Ala Lys Arg Pro Arg Ala Lys Arg Asp Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Furin Inhibitor

<400> SEQUENCE: 10

Cys Lys Lys Val Ala Lys Arg Pro Arg Ala Lys Arg Asp Leu
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Furin Inhibitor L6R (hexa-L-arginine)

<400> SEQUENCE: 11

Arg Arg Arg Arg Arg Arg
1               5

<210> SEQ ID NO 12
<211> LENGTH: 10
<212> TYPE: PRT
<213> ORGANISM: Artificial Sequence
<220> FEATURE:
<223> OTHER INFORMATION: Kallikrein Inhibitor

<400> SEQUENCE: 12

Ser Arg Phe Lys Val Trp Trp Ala Ala Gly
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: Kallikrein Inhibitor

<400> SEQUENCE: 13

Ala Ala Arg Arg Pro Phe Pro Ala Pro Ser
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Kallikrein Inhibitor

<400> SEQUENCE: 14

Pro Ala Arg Arg Pro Phe Pro Val Thr Ala
1               5                   10

<210> SEQ ID NO 15
<211> LENGTH: 16
<212> TYPE: PRT
<213> ORGANISM: Artificial Sequence
<220> FEATURE:
<223> OTHER INFORMATION: Pepsinogen 1-16

<400> SEQUENCE: 15

Leu Val Lys Val Pro Leu Val Arg Lys Lys Ser Leu Arg Gln Asn Leu
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: Pepsinogen 1-12

<400> SEQUENCE: 16

Leu Val Lys Val Pro Leu Val Arg Lys Lys Ser Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Pepsinogen 1-12 4-7 substitution (II) [Gly4,5]

<400> SEQUENCE: 17

Leu Val Lys Gly Gly Leu Val Arg Lys Lys Ser Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Pepsinogen 1-12 4-7 substitution (III) [Gly6,7]

<400> SEQUENCE: 18

Leu Val Lys Val Pro Gly Gly Arg Lys Lys Ser Leu
1               5                   10

<210> SEQ ID NO 19
```

-continued

```
<211> LENGTH: 12
<212> TYPE: PRT
<213> ORGANISM: Artificial Sequence
<220> FEATURE:
<223> OTHER INFORMATION: Pepsinogen 1-12 4-7 substitution (IV) [GIy4-7]

<400> SEQUENCE: 19

Leu Val Lys Gly Gly Gly Gly Arg Lys Lys Ser Leu
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Sunflower trysin inhibitor SFTI-1

<400> SEQUENCE: 20

Gly Arg Cys Thr Lys Ser Ile Pro Pro Ile Cys Phe Pro Asp
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Odorrana trypsin inhibitor

<400> SEQUENCE: 21

Ala Val Asn Ile Pro Phe Lys Val His Phe Arg Cys Lys Ala Ala Phe
1               5                   10                  15

Cys

<210> SEQ ID NO 22
<211> LENGTH: 61
<212> TYPE: PRT
<213> ORGANISM: Artificial Sequence
<220> FEATURE:
<223> OTHER INFORMATION: Ascaris chymotrypsin elastase inhibitor

<400> SEQUENCE: 22

Gly Gln Glu Ser Cys Gly Pro Asn Glu Val Trp Thr Glu Cys Thr Gly
1               5                   10                  15

Cys Glu Met Lys Cys Gly Pro Asp Glu Asn Thr Pro Cys Pro Leu Met
            20                  25                  30

Cys Arg Arg Pro Ser Cys Glu Cys Ser Pro Gly Arg Gly Met Arg Arg
        35                  40                  45

Thr Asn Asp Gly Lys Cys Ile Pro Ala Ser Gln Cys Pro
    50                  55                  60

<210> SEQ ID NO 23
<211> LENGTH: 66
<212> TYPE: PRT
<213> ORGANISM: Artificial Sequence
<220> FEATURE:
<223> OTHER INFORMATION: Ascaris trypsin inhibitor

<400> SEQUENCE: 23

Glu Ala Glu Lys Cys Asx Glx Glx Pro Gly Trp Thr Lys Gly Gly Cys
1               5                   10                  15

Glu Thr Cys Gly Cys Ala Gln Lys Ile Val Pro Cys Thr Arg Glu Thr
            20                  25                  30

Lys Pro Asn Pro Gln Cys Pro Arg Lys Gln Cys Cys Ile Ala Ser Ala
        35                  40                  45
```

```
Gly Phe Val Arg Asp Ala Gln Gly Asn Cys Ile Lys Phe Glu Asp Cys
        50                  55                  60

Pro Lys
65

<210> SEQ ID NO 24
<211> LENGTH: 62
<212> TYPE: PRT
<213> ORGANISM: Artificial Sequence
<220> FEATURE:
<223> OTHER INFORMATION: Ascaris trypsin inhibitor

<400> SEQUENCE: 24

Glu Ala Glu Lys Cys Thr Lys Pro Asn Glu Gln Trp Thr Lys Cys Gly
1               5                   10                  15

Gly Cys Glu Gly Thr Cys Ala Gln Lys Ile Val Pro Cys Thr Arg Glu
            20                  25                  30

Cys Lys Pro Pro Arg Cys Glu Cys Ile Ala Ser Ala Gly Phe Val Arg
        35                  40                  45

Asp Ala Gln Gly Asn Cys Ile Lys Phe Glu Asp Cys Pro Lys
    50                  55                  60

<210> SEQ ID NO 25
<211> LENGTH: 101
<212> TYPE: PRT
<213> ORGANISM: Artificial Sequence
<220> FEATURE:
<223> OTHER INFORMATION: Onion trypsin inhibitor

<400> SEQUENCE: 25

Met Lys Ala Ala Leu Val Ile Phe Leu Leu Ile Ala Met Leu Gly Val
1               5                   10                  15

Leu Ala Ala Glu Ala Tyr Pro Asn Leu Arg Gln Val Val Thr Gly
            20                  25                  30

Asp Glu Glu Gly Gly Cys Cys Asp Ser Cys Gly Ser Cys Asp Arg
        35                  40                  45

Arg Ala Pro Asp Leu Ala Arg Cys Glu Cys Arg Asp Val Val Thr Ser
    50                  55                  60

Cys Gly Pro Gly Cys Lys Arg Cys Glu Glu Ala Asp Leu Asp Leu Asn
65                  70                  75                  80

Pro Pro Arg Tyr Val Cys Lys Asp Met Ser Phe His Ser Cys Gln Thr
                85                  90                  95

Arg Cys Ser Ile Leu
            100

<210> SEQ ID NO 26
<211> LENGTH: 84
<212> TYPE: PRT
<213> ORGANISM: Artificial Sequence
<220> FEATURE:
<223> OTHER INFORMATION: Barley chymotrypsin inhibitor 2

<400> SEQUENCE: 26

Met Ser Ser Met Glu Lys Lys Pro Glu Gly Val Asn Ile Gly Ala Gly
1               5                   10                  15

Asp Arg Gln Asn Gln Lys Thr Glu Trp Pro Glu Leu Val Gly Lys Ser
            20                  25                  30

Val Glu Glu Ala Lys Lys Val Ile Leu Gln Asp Lys Pro Ala Ala Gln
        35                  40                  45
```

-continued

```
Ile Ile Val Leu Pro Val Gly Thr Ile Val Thr Met Glu Tyr Arg Ile
 50                  55                  60

Asp Arg Val Arg Leu Phe Val Asp Arg Leu Asp Asn Ile Ala Gln Val
 65                  70                  75                  80

Pro Arg Val Gly

<210> SEQ ID NO 27
<211> LENGTH: 4
<212> TYPE: PRT
<213> ORGANISM: Artificial Sequence
<220> FEATURE:
<223> OTHER INFORMATION: Thrombin Inhibitor

<400> SEQUENCE: 27

Ile Gln Pro Arg
1

<210> SEQ ID NO 28
<211> LENGTH: 6
<212> TYPE: PRT
<213> ORGANISM: Artificial Sequence
<220> FEATURE:
<223> OTHER INFORMATION: Thrombin Inhibitor

<400> SEQUENCE: 28

Gly Ser Ala Val Pro Arg
1               5

<210> SEQ ID NO 29
<211> LENGTH: 54
<212> TYPE: PRT
<213> ORGANISM: Artificial Sequence
<220> FEATURE:
<223> OTHER INFORMATION: Furin Activated Furin Inhibitor
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 29

Thr Lys Lys Val Ala Lys Arg Pro Arg Ala Lys Arg Ala Ala Arg Xaa
1               5                   10                  15

Lys Arg Ser Xaa Thr Lys Lys Val Ala Lys Arg Pro Arg Ala Lys Arg
            20                  25                  30

Ala Ala Arg Xaa Lys Arg Ser Xaa Thr Lys Lys Val Ala Lys Arg Pro
        35                  40                  45

Arg Ala Lys Arg Ala Ala
    50

<210> SEQ ID NO 30
<211> LENGTH: 6
<212> TYPE: PRT
<213> ORGANISM: Artificial Sequence
<220> FEATURE:
<223> OTHER INFORMATION: Factor Xa
```

```
<400> SEQUENCE: 30

Ile Glu Gly Arg Ser Val
1               5

<210> SEQ ID NO 31
<211> LENGTH: 6
<212> TYPE: PRT
<213> ORGANISM: Artificial Sequence
<220> FEATURE:
<223> OTHER INFORMATION: Furin
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 31

Arg Xaa Lys Arg Ser Xaa
1               5

<210> SEQ ID NO 32
<211> LENGTH: 6
<212> TYPE: PRT
<213> ORGANISM: Artificial Sequence
<220> FEATURE:
<223> OTHER INFORMATION: Plasminogen activator
<220> FEATURE:
<221> NAME/KEY: misc_feature
<222> LOCATION: (1)..(2)
<223> OTHER INFORMATION: Xaa can be any naturally occurring amino acid

<400> SEQUENCE: 32

Xaa Xaa Arg Arg Ile Asn
1               5

<210> SEQ ID NO 33
<211> LENGTH: 6
<212> TYPE: PRT
<213> ORGANISM: Artificial Sequence
<220> FEATURE:
<223> OTHER INFORMATION: Urokinase
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 33

Xaa Ser Gly Arg Xaa Arg
1               5

<210> SEQ ID NO 34
<211> LENGTH: 7
<212> TYPE: PRT
<213> ORGANISM: Artificial Sequence
<220> FEATURE:
<223> OTHER INFORMATION: MMP1
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
```

```
<223> OTHER INFORMATION: Xaa can be any naturally occurring amino acid

<400> SEQUENCE: 34

Gly Pro Xaa Gly Leu Xaa Gly
1               5

<210> SEQ ID NO 35
<211> LENGTH: 7
<212> TYPE: PRT
<213> ORGANISM: Artificial Sequence
<220> FEATURE:
<223> OTHER INFORMATION: MMP8

<400> SEQUENCE: 35

Gly Pro Gln Gly Leu Arg Gly
1               5

<210> SEQ ID NO 36
<211> LENGTH: 7
<212> TYPE: PRT
<213> ORGANISM: Artificial Sequence
<220> FEATURE:
<223> OTHER INFORMATION: MMP 13
<220> FEATURE:
<221> NAME/KEY: misc_feature
<222> LOCATION: (6)..(6)
<223> OTHER INFORMATION: Xaa can be any naturally occurring amino acid

<400> SEQUENCE: 36

Gly Pro Pro Gly Leu Xaa Gly
1               5

<210> SEQ ID NO 37
<211> LENGTH: 8
<212> TYPE: PRT
<213> ORGANISM: Artificial Sequence
<220> FEATURE:
<223> OTHER INFORMATION: Membrane matrix metalloprotease 1
<220> FEATURE:
<221> NAME/KEY: misc_feature
<222> LOCATION: (8)..(8)
<223> OTHER INFORMATION: Xaa can be any naturally occurring amino acid

<400> SEQUENCE: 37

Leu Pro Ala Gly Leu Val Leu Xaa
1               5

<210> SEQ ID NO 38
<211> LENGTH: 7
<212> TYPE: PRT
<213> ORGANISM: Artificial Sequence
<220> FEATURE:
<223> OTHER INFORMATION: PSA

<400> SEQUENCE: 38

Ser Ser Gln Tyr Ser Ser Asn
1               5

<210> SEQ ID NO 39
<211> LENGTH: 8
<212> TYPE: PRT
<213> ORGANISM: Artificial Sequence
<220> FEATURE:
<223> OTHER INFORMATION: Kallikrein 2

<400> SEQUENCE: 39

Gly Gly Leu Arg Ser Gly Gly Gly
1               5
```

```
<210> SEQ ID NO 40
<211> LENGTH: 7
<212> TYPE: PRT
<213> ORGANISM: Artificial Sequence
<220> FEATURE:
<223> OTHER INFORMATION: Granzyme A
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 40

Thr Xaa Xaa Pro Arg Ser Xaa
1               5

<210> SEQ ID NO 41
<211> LENGTH: 6
<212> TYPE: PRT
<213> ORGANISM: Artificial Sequence
<220> FEATURE:
<223> OTHER INFORMATION: Granzyme B
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 41

Val Glu Xaa Asp Ser Xaa
1               5

<210> SEQ ID NO 42
<211> LENGTH: 5
<212> TYPE: PRT
<213> ORGANISM: Artificial Sequence
<220> FEATURE:
<223> OTHER INFORMATION: Granzyme M
<220> FEATURE:
<221> NAME/KEY: misc_feature
<222> LOCATION: (5)..(5)
<223> OTHER INFORMATION: Xaa can be any naturally occurring amino acid

<400> SEQUENCE: 42

Lys Val Pro Leu Xaa
1               5

<210> SEQ ID NO 43
<211> LENGTH: 7
<212> TYPE: PRT
<213> ORGANISM: Artificial Sequence
<220> FEATURE:
<223> OTHER INFORMATION: Cathespin B
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 43

Xaa Leu Arg Xaa Xaa Gly Gly
```

```
1               5
```

```
<210> SEQ ID NO 44
<211> LENGTH: 7
<212> TYPE: PRT
<213> ORGANISM: Artificial Sequence
<220> FEATURE:
<223> OTHER INFORMATION: Cathespin S
<220> FEATURE:
<221> NAME/KEY: misc_feature
<222> LOCATION: (6)..(6)
<223> OTHER INFORMATION: Xaa can be any naturally occurring amino acid

<400> SEQUENCE: 44

Ser Gly Phe Arg Ser Xaa Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Thrombin
<220> FEATURE:
<221> NAME/KEY: misc_feature
<222> LOCATION: (7)..(7)
<223> OTHER INFORMATION: Xaa can be any naturally occurring amino acid

<400> SEQUENCE: 45

Ala Gly Pro Arg Ser Leu Xaa
1               5

<210> SEQ ID NO 46
<211> LENGTH: 6
<212> TYPE: PRT
<213> ORGANISM: Artificial Sequence
<220> FEATURE:
<223> OTHER INFORMATION: Plasmin
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 46

Ala Xaa Leu Lys Ser Xaa
1               5

<210> SEQ ID NO 47
<211> LENGTH: 6
<212> TYPE: PRT
<213> ORGANISM: Artificial Sequence
<220> FEATURE:
<223> OTHER INFORMATION: Plasminogen
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 47

Ala Xaa Leu Lys Ser Xaa
1               5
```

PROTEASE INHIBITOR COMBINATION WITH THERAPEUTIC PROTEINS INCLUDING ANTIBODIES

CROSS REFERENCE TO RELATED APPLICATIONS

The present application is a Division of U.S. patent application Ser. No. 13/024,179, filed Feb. 9, 2011, which claims benefit of priority under 35 U.S.C. § 119(e) from U.S. Provisional Patent Application No. 61/302,763, filed Feb. 9, 2010, each of which is expressly incorporated in its entirety.

FIELD OF THE INVENTION

This invention is related to the field of therapeutic delivery systems, and methods for improving the delivery, stability and efficacy of protein therapeutics.

BACKGROUND OF THE INVENTION

Citation or identification of any reference herein, or any section of this application shall not be construed as an admission that such reference is available as prior art to the present application. The disclosures of each of these publications in their entireties are hereby incorporated by reference in their entirety in this application, and shall be treated as if the entirety thereof forms a part of this application.

Once a rarely used subset of medical treatments, protein therapeutics have increased dramatically in number and frequency of use since the introduction of the first recombinant protein therapeutic, human insulin, 25 years ago. Protein therapeutics already have a significant role in almost every field of medicine, but this role is still only in its infancy. (Leader et al., 2008, Protein therapeutics: a summary and pharmacological classification Nature Reviews Drug Discovery 7, 21-39).

Targeted monoclonal antibodies comprise a major form of therapeutic proteins. Targeting monoclonal antibodies to the tumor can result in the destruction of the tumor cells by antibody-dependent cellular cytotoxicity or complement-dependent cytotoxicity. Similarly, targeting cytokines or immunomodulatory molecules either by bispecific scFv or antibody-ligand fusion proteins to the tumor modulates the immune response against the tumor. In addition, antibody-ligand fusion proteins can induce apoptosis to targeted cells as well as bystander cells by, for example, presenting FasL. A more direct approach to kill the targeted cell is the conjugation of cytotoxic drugs, toxins or radionuclides to the monoclonal antibodies. The antibody-directed enzyme prodrug therapy (ADEPT) approach specifically aims at causing bystander effects by targeting enzymes to the tumor cell and delivering a prodrug that is converted to a chemotherapeutic by the targeted enzyme. (Schrama et al., 2006, Antibody targeted drugs as cancer therapeutics, *Nature Reviews Drug Discovery* 5, 147-159). Examples of monoclonal antibody therapeutics are shown in Table I. However, means to enhance their protease stability have not been provided, particularly for tumor-targeted antibodies.

TABLE I

Monoclonal antibody therapeutics approved for clinical use. From: An, 2008, Antibody Therapeutics - a mini review. Trends in Bio/Pharmaceutical Industry 2: 24-29.

| Generic Name Trade Name Manufacturer | Launch Date | Therapy Area | Major Indication | Target | Protein Form/Isotype | Delivery | Reference |
|---|---|---|---|---|---|---|---|
| Muromonab Orthoclone/OKT3 Johnson & Johnson | 1986 | AIID | Transplant rejection | CD3 | Murine IgG2a | IV | (16) |
| Abciximab ReoPro Eli Lilly | 1995 | CV | Cardiovascular disease | CD41 | Chimeric Fab | IV | (8) |
| Rituximab Rituxan/MabThera Genentech/Roche | 1997 | Oncology | Non-Hodgkin's Lymphoma | CD20 | Chimeric IgG1 | IV | (17) |
| Daclizumab Zenapax Roche | 1997 | AIID | Transplant rejection | CD25 | Humanized IgG1 | IV | (9) |
| Basiliximab Simulect Novartis | 1998 | AIID | Transplant rejection | CD25 | Chimeric IgG1 | IV | (18) |
| Infliximab Remicade Centocor | 1998 | AIID | Rheumatoid arthritis | TNF alpha | Chimeric IgG1 | IV | (19) |
| Palivizumab Synagis MedImmune | 1998 | ID | Respiratory syncytial virus | RSV F-protein | Chimeric IgG1 | IM | (20) |
| Trastuzumab Herceptin Genentech | 1998 | Oncology | Breast cancer | Her2 | Humanized IgG1 | IV | (21) |
| Gemtuzumab/ozogamicin Mylotarg Wyeth | 2000 | Oncology | Acute myclogenous leukemia | CD33 | Humanized IgG4 conjugated with ozogamicin | IV | (22) |
| Alemtuzumab Campath Bayer-Schering | 2001 | Oncology | Chronic lymphocytic leukemia | CD52 | Humanized IgG1 | IV | (23) |
| Ibritumomab tiuxetan Zevalin Biogen/Idec | 2002 | Oncology | Non-Hodgkin's Lymphoma | CD20 | Murine IgG1 conjugated with Yttrium 90 | IV | (24) |

TABLE I-continued

Monoclonal antibody therapeutics approved for clinical use. From: An, 2008,
Antibody Therapeutics - a mini review. Trends in Bio/Pharmaceutical Industry 2: 24-29.

| Generic Name Trade Name Manufacturer | Launch Date | Therapy Area | Major Indication | Target | Protein Form/Isotype | Delivery | Reference |
|---|---|---|---|---|---|---|---|
| Omalizumab Xolair Genentech/Novartis | 2003 | Respiratory | Asthma | IgE | Humanized IgG1 | SC | (25) |
| Efalizumab Raptiva Genentech | 2003 | AIID | Psoriasis | CD11A | Humanized IgG1 | SC | (26) |
| Tositumomab Bexxar GSK | 2003 | Oncology | Non-Hodgkin's Lymphoma | CD20 | Murine IgG2a conjugated with Iodine-131 | IV | (27) |
| Adalimumab Humira Abbott | 2003 | AIID | Rheumatoid arthritis | TNF alpha | Human IgG1 | SC | (11) |
| Cetuximab Erbitux ImClone/BMS | 2003 | Oncology | Colorectal cancer | EGFR | Chimeric IgG1 | IV | (28) |
| I-131 ch-TNT Shanghai Medipharm Biotech Co. | 2003 | Oncology | Advanced lung cancer | Intracellular DNA in tumors | Chimeric IgG1 conjugated with I-131 | IV | (29) |
| Bevacizumab Avastin Genentech | 2004 | Oncology | Colorectal and non-small cell lung cancer | VEGF | Humanized IgG1 | IV | (30) |
| Natalizumab Tysabri Biogen IDEC/Elan | 2004 | CNS/AIID | Multiple sclerosis | VLA4 | humanized IgG1 | IV | (31) |
| Tocilizumab Actemra Roche/Chugai | 2005 | AIID | Castleman's disease | IL-6R | Humanized IgG1 | IV | (32) |
| Ranibizumab Lucentis Genentech/Novartis | 2006 | Ophthalmology | Wet age-related macular degeneration | VEGF | Humanized mab fragment of Avastin | Injection into the eye | (3) |
| Panitumumab Vectibix Amgen | 2006 | Oncology | Colorectal cancer | EGFR | Human IgG2 | IV | (33) |
| Certolizumab pegol Cimzia UCB-Schwarz | 2007 | AIID | Rheumatoid arthritis | TNF alpha | PEGylated Fragment | SC | (4) |
| Eculizumab Soliris Alexion | 2007 | Hematology | PNH (chronic hemolysis) | C5a | Humanized IgG2/IgG4 hybrid | IV | (34) |

SUMMARY OF THE INVENTION

Protease inhibitors together with protease sensitive therapeutics are provided. Therefore, the localized in vivo activity of protease-sensitive drugs will be increased. Likewise, the physical region of activity for a highly protease sensitive peptide agent will be generally limited to the region in which both the protease inhibitor and peptide are present at sufficient concentrations.

The polymeric protease activated protease inhibitors can be homo- or hetero-inhibitor polymers, and/or homo- or hetero-protease cleavage site polymers. Combination with the protease inhibitors with the protease sensitive therapeutic enhances the intact, active molecule local-regional or targeted cell or tissue concentration, peak concentration and/or duration of the therapeutic exposure, thereby increasing its therapeutic efficacy. The protease inhibitors are particularly useful for tumor-targeted therapies and for vaccines.

The present invention comprises systems, compositions, and methods for using protease inhibitors together with protease sensitive therapeutics. The protease inhibitors may be ionically bound the protease sensitive therapeutic, covalently bound (e.g., connected through a covalent bond), or unbound. The protease inhibitors include monomeric protease inhibitors, and polymeric inhibitors where the inhibitors are themselves protease activated, or the protease inhibitors may be activated or activated in some other way. The protease cleavage site may be for the same protease that the peptide inactivates, and thus, the protease activates its own inhibitor. The protease inhibitor may be of a competitive or non-competitive type. The protease cleavage site may also be for a protease other than for the protease inhibitor, thus deactivating another protease. Multiple protease inhibitor peptides may be used in-frame with multiple protease cleavage signals (polymeric protease activated protease inhibitors). The polymeric protease activated protease inhibitors can be homo- or hetero-inhibitor polymers, and/or homo- or hetero-protease cleavage site polymers.

Combination of a protease inhibitor with a protease sensitive therapeutic may enhance the intact, active molecule local-regional or targeted cell or tissue concentration, peak concentration and/or duration of the therapeutic exposure, thereby increasing its therapeutic efficacy.

The protease inhibitors are particularly useful for tumor-targeted therapies, which for example include the protease sensitive therapeutic.

The compositions comprising a protease inhibitor and protease-sensitive agent may be administered in traditional manner through oral, transcutaneous, transmucosal, intravenous, intramuscular, intraperitoneal, intrathecal manner, or in situ administration in a solid or liquid form, encapsulated in a polymer or liposome, or employing known administration technologies. On the other hand, the protease inhibitor and/or protease sensitive agent may be produced by a genetically engineered cell or colony of cells, such as prokaryotic cells, e.g., *Salmonella, E. coli*, or *mycoplasma* sp., or eukaryotic cells, such as autologous human cells in the case of a human therapy or diagnostic aid.

DETAILED DESCRIPTION OF THE INVENTION

Figure 1:
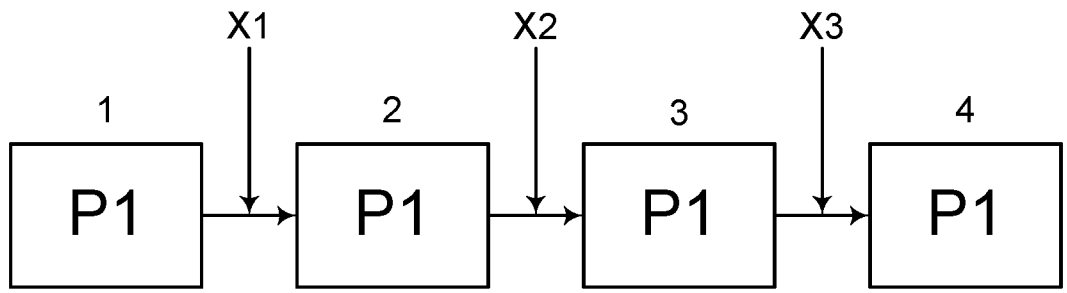
FIG. 1 shows a polymeric protease-activated protease inhibitor.

The present invention provides, according to various embodiments, improved protein therapeutics with increased circulation (enhanced pharmacokinetics), longer half-lives and decreased degradation. In a preferred embodiment, the protein therapeutic is an antitumor antibody.

Protease Sensitivity

Therapeutic proteins are typically inherently sensitive to extracellular proteases. Proteases may be classified by several different systems, for example, into six groups: serine proteases, threonine proteases, cysteine proteases, aspartate proteases, metalloproteases and glutamic acid proteases. Alternatively, proteases may be classified by the optimal pH in which they are active: acid proteases, neutral proteases, and basic proteases (or alkaline proteases). Many proteases are over-expressed within tumors (Edwards et al. (eds) 2008, The Cancer Degradome: Proteases and Cancer Biology, Springer, 926 pp.) including tissue plasminogen activator, activated protein C, factor Xa, granzyme (A, B, M), cathepsins (e.g., cathepsin B and S), thrombin, plasmin, urokinase, matrix metaloproteaes (types 1-26) membrane matrix metalloproteases (types 1-4), prostate specific antigens (PSA; kallikrein 3-related peptidase), kallikrein 2, elastin, trypsin, chymotrypsin.

A variety of protease assays are known to those skilled in the art. Many protease assays are commercially available, such as the QuantiCleave Fluorescent Protease Assay Kit, and QuantiCleave Protease Assay Kit II (Thermo/Fisher, Rockford, Ill.), Protease Assay Kit (G Biosciences, Maryland Heights, Mo.), PepTag Protease Assay (Promega, Madison, Wis.; 1993 Promega Notes Magazine 44: 2), Viral Protease Assay Kits (AnaSpec, Fremont, Calif.), Protease Assay Kit from Calbiochem (Calbiochem, San Diego, Calif.).

Standard laboratory techniques to measure protease activity, and thus the reduced activity of protease inhibitors, include densitometric, spectrophotometric, colorimetric and fluorometric assays, sodium dodecyl sulfate (SDS) polyacrylamide gel electrophoresis (PAGE), two dimensional SDS-PAGE, high pressure liquid chromatography (HPLC) and mass spectroscopy (mass-spec). Examples of proteases and their cleavage signals are shown in Table 2.

Protease cleavage sites are defined in the MEROPS database (Rawlings et al., 2010, MEROPS: The Peptidase Database, Nucleic Acids Res. 2010 (Database issue):D227-33. It will be understood to those skilled in the arts that many proteases do not have strict sequence recognition sites, but rather have sequence preferences and/or frequencies. The MEROPS site depicts the preferences with a weighted pictogram and a table which lists frequencies of occurrence within a cleavage sequence. The table a non-limiting list proteases of tumors, the MEROPS sequence specification, and a simplified representative of an amino acid one letter code recognition sequence (where X is any amino acid) and the cleavage signal is given by a downward arrow) is presented in Table 2.

TABLE 2

Examples of protease cleavage sequences.

| Protease | MEROPS Sequence Designation | Simplified Representative Sequence Designation |
|---|---|---|
| Factor Xa | ia/e/Gfp/R⁺sti/vfs/—/g | (IEGR↓SV) SEQ ID NO: 30 |
| Furin | R/—/Kr/R⁺s/—/—/— | (RXKR↓SX) SEQ ID NO: 31 |
| Plasminogen activator | —/—/—/R⁺R/iv/N/— | (XXR↓RIN) SEQ ID NO: 32 |
| Urokinase | —/sg/Gs/Rk⁺—/r/—/— | (XSGR↓XR) SEQ ID NO: 33 |
| MMP1 | —/pa/—/g⁺li/—/—/— | (GPXG↓LXG) SEQ ID NO: 34 |
| MMP8 | g/Pas/—/g⁺l/—/g/— | (GPQG↓LRG) SEQ ID NO: 35 |
| MMP 13 | g/P/—/g⁺l/—/ga/— | (GPPG↓LXG) SEQ ID NO: 36 |
| Membrane matrix metalloprotease 1 | —/p/—/—⁺l/—/—/— | (LPAG↓LVLX) SEQ ID NO: 37 |
| PSA | si/sq/—/yq⁺s/s/—/— | (SSQY↓SSN) SEQ ID NO: 38 |
| Kallikrein 2 | g/—/—/R⁺—/—/—/gs | (GGLR↓SGGG) SEQ ID NO: 39 |
| Granzyme A | t/—/—/RK⁺sa/—/—/— | (TXXPR↓SX) SEQ ID NO: 40 |
| Granzyme B | v/—/—/D⁺—/—/—/— | (VEXD↓SX) SEQ ID NO: 41 |
| Granzyme M | Ka/vaye/Pa/LM⁺—/—/—/— | (KVPL↓X) SEQ ID NO: 42 |
| Cathepsin B | —/—/l/r⁺—/—/g/— | (XLR↓XXGG) SEQ ID NO: 43 |
| Cathepsin S | —/—/flv/r⁺—/—/—/— | (SGFR↓SXG) SEQ ID NO: 44 |
| Thrombin | —/—/pla/R⁺sag/—/—/— | (AGPR↓SLX) SEQ ID NO: 45 |
| Plasmin | —/—/—/KR⁺—/—/—/— | (AXLK↓SX) SEQ ID NO: 46 |
| Plasminogen | /—/—/KR⁺—/—/—/— | (AXLK↓SX) SEQ ID NO: 47 |

The MEROPS database can be used to identify which proteases to inhibit, by analysis of a particular effector protein and the cleavage sites it contains. Comparison with the target tissue, eg Edwards et al. (eds) 2008, The Cancer Degradome: Proteases and Cancer Biology, Springer, 926 pp is also used to inform the choice. Alternatively, 2-dimentional gel electrophoresis and protein sequencing of radiolabled peptides incubated with the target tumor can be used to identify which amino acids are being cleaved in a therapeutic protein, and therefore which protease inhibitors to use.

Protease Inhibitors

Protease inhibitors usable in accordance herewith are preferably based on known polypeptide inhibitors. The inhibitors include both synthetic peptides and naturally occurring, endogenous peptides. Classes of protease inhibitors include: cysteine protease inhibitors, serine protease inhibitors (serpins), trypsin inhibitors, Kunitz STI protease inhibitor, threonine protease inhibitors, aspartic protease inhibitors, metalloprotease inhibitors. Protease inhibitors can also be classified by mechanism of action as suicide inhibitors, transition state inhibitors, protein protease inhibitor (see serpins) and chelating agents. The protease inhibitors are typically protein or polypeptide inhibitors that are activated by protease cleavage, resulting in a time-released "depot" effect.

The C-terminal sequences may provide a free protease inhibitor. The cleavage site may be for the same protease that the peptide inactivates. Thus, the protease activates its own inhibitor. The protease cleavage site may also be for a protease other than for the protease inhibitor, thus deactivating another protease. Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have inhibitors for the same or different proteases, respectively), and/or homo- or hetero-protease cleavage polymers (i.e., have the same or different protease cleavage sites). Examples of proteases upregulated within tumors include: tissue plasminogen activator, activated protein C, factor Xa, granzyme (A, B, M), cathepsin, thrombin, plasmin, urokinase, matrix metalloproteases, prostate specific antigen (PSA) and kallikrein 2 (e.g., Edwards et al. (eds) 2008, The Cancer Degradome: Proteases and Cancer Biology, Springer, 926 pp.), as well as proteases of lysosomes and the gut.

Protease inhibitors have been reviewed by Laskowski and Kato, 1980, (Annual Review of Biochemistry 49: 593-626), expressly incorporated by reference herein. Serine proteases inhibitors, the largest group, include 1) bovine pancreatic trypsin inhibitor (Kunitz) family, 2) pancreatic secretory trypsin inhibitor (Kazal) family, 3) *Streptomyces* subtilisin inhibitor family, 4) soybean trypsin inhibitor (Kunitz) family, 5) soybean proteinase inhibitor (Bowman-Birk) family 6) potato I inhibitor family, 7) potato II inhibitor family, 8) *Ascaris* trypsin inhibitor family, and 9) others. Protease inhibitors have also been grouped within the MEROPS peptidase database (Rawlings et al., 2008 Nucleic Acids Res. 36 Database issue, D320-325).

Specific examples of protease inhibitors that may be expressed as complete proteins or peptide fragments corresponding to the active inhibitory site include but are not limited to aprotinin, cathepsin inhibitor peptide sc-3130, *Neisseria* protease inhibitor, lymphocyte protease inhibitor, maspin, matrix metalloprotease inhibitors, macroglobulins, antithrombin, equistatin, Bowman-Birk inhbitor family, ovomucoid, ovoinhibitor-proteinase inhibitors from avian serum, dog submandibular inhibitors, inter-a-trypsin inhibitors from mammalian serum, chelonianin from turtle egg white, soybean trypsin inhibitor (Kunitz), secretory trypsin inhibitors (Kazal) ai-proteinase inhibitor, *Streptomyces* subtilisin inhibitor, plasminostreptin, plasmin inhibitor, factor Xa inhibitor, coelenterate protease inhibitors, protease inhibitor anticoagulants, ixolaris, human Serpins (SerpinA1 (alpha 1-antitrypsin), SerpinA2, SerpinA3, SerpinA4, SerpinA5, SerpinA6, SerpinA7, SerpinA8, SerpinA9, SerpinA10, SerpinA11, SerpinA12, SerpinA13, SerpinB1, SerpinB2, SerpinB3, SerpinB4, SerpinB5, SerpinB6, SerpinB7, SerpinB8, SerpinC1 (antithrombin), SerpinD1, SerpinE1, SerpinE2, SerpinF1, SerpinF2, SerpinG1, SerpinNI1, SerpinNI2), cowpea trypsin inhibitor, onion trypsin inhibitor, alpha 1-antitrypsin, *Ascaris* trypsin and pepsin inhibitors, lipocalins, CI inhibitor, plasminogen-activator inhibitor, collagenase inhibitor, Acp62F from *Drosophila*, bombina trypsin inhibitor, *bombyx* subtilisin inhibitor, von Willebrand factor, leukocyte secretory protease inhibitor. Short peptide inhibitors of protease are preferred. Many protease inhibitors have one or more disulfide bonds. Fusion to thioredoxin (trxA) is known to improve protease inhibitor activity (e.g., Furuki et al., 2007, Fukuoka University Science Reports 37: 37-44). Fusion to glutathione-S transferase (GST) and co-expression with disulfide bond isomerase (DsbA) or nusA (Harrison 2000, Expression of soluble heterologous proteins via fusion with NusA protein. *inNovations* 11: 4-7) are also known to improve solubility. Examples of the peptide sequences of short peptide inhibitors is shown in Table 3.

TABLE 3

Sequences of short peptide protease inhibitors

| Protease Inhibitor | Protease(s) inhibited | Protein/Peptide Name and/or Peptide Sequence |
|---|---|---|
| Leupeptin | calpain, plasmin, trypsin, papain, and cathepsin B | Leupeptin |
| Aprotinin | Trypsin Plasmin Tissue kallikrein | RPDFC LEPPY TGPCK ARIIR YFYNA KAGLC QTFVY GGCRA KRNNF KSAED CMRTC GGA SEQ ID NO: 001 |
| Aprotinin homologues | Variable | Brinkmann et al, 1991 Eur J. Biochem 202: 95-99 |
| Protease Inhibitor 15 | Trypsin | Synthetic peptide: CFPGVTSNYLYWFK SEQ ID NO: 002, corresponding to amino acids 245-258 of human protease inhibitor. |
| Tissue protease inhibitor | Serine protease inhibitor, Kazal type 1, mature | DSLGREAKCYNELNGCTKIYDPVCGTDGNTYPNECVLCF ENRKRQTSILIQKSGPC SEQ ID NO: 003 |
| Furin inhibitors | Furin | PAAATVTKKVAKSPKKAKAAKPKKAAKSAAKAVKPK SEQ ID NO: 004 TKKVAKRPRAKRAA SEQ ID NO: 005 TKKVAKRPRAKRDL SEQ ID NO: 006 GKRPRAKRA SEQ ID NO: 007 CKRPRAKRDL SEQ ID NO: 008 CVAKRPRAKRDL SEQ ID NO: 009 CKKVAKRPRAKRDL SEQ ID NO: 010 RRRRRR L6R (hexa-L-arginine) SEQ ID NO: 011 |
| Kallikrein Inhibitors | Kallikrein 2 | SRFKVWWAAG SEQ ID NO: 012 AARRPFPAPS SEQ ID NO: 013 PARRPFPVTA SEQ ID NO: 014 |

TABLE 3-continued

Sequences of short peptide protease inhibitors

| Protease Inhibitor | Protease(s) inhibited | Protein/Peptide Name and/or Peptide Sequence |
|---|---|---|
| Pepsinogen 1-16 | Pepsin | LVKVPLVRKKSLRQNL SEQ ID NO: 015<br>Dunn et al., 1983 Biochem J 209: 355-362 |
| Pepsinogen 1-12 | Pepsin | LVKVPLVRKKSL SEQ ID NO: 016<br>Dunn et al., 1983 Biochem J 209: 355-362 |
| Pepsinogen 1-12 4-7 substitution | Pepsin | LVKGGLVRKKSL (II) [Gly4,5] SEQ ID NO: 017<br>LVKVPGGRKKSL (III) [Gly6,7] SEQ ID NO: 018<br>LVKGGGGRKKSL (IV) [Gly4-7] SEQ ID NO: 019<br>Dunn et al., 1983 Biochem J 209: 355-362 |
| Sunflower trysin inhibitor SFTI-1 | Trypsin | GRCTKSIPPICFPD SEQ ID NO: 020 |
| Odorrana trypsin inhibitor | Trypsin | AVNIPFKVHFRCKAAFC SEQ ID NO: 021 |
| Ascaris chymotrypsin elastase inhibitor | Chymtrypsin Elastase | GQESCGPNEV WTECTGCEMK CGPDENTPCP LMCRRPSCEC SPGRGMRRTN DGKCIPASQCP SEQ ID NO: 022 |
| Ascaris trypsin inhibitor | Trypsin | EAEKCBZZPG WTKGGCETCG CAQKIVPCTR ETKPNPQCPR KQCCIASAGF VRDAQGNCIK FEDCPK SEQ ID NO: 023 |
| Ascaris trypsin inhibitor | Trypsin | EAEKCTKPNE QWTKCGGCEG TCAQKIVPCT RECKPPRCEC IASAGFVRDA QGNCIKFEDC PK SEQ ID NO: 024 |
| Onion trypsin inhibitor | Trypsin | MKAALVIFLL IAMLGVLAAE AYPNLRQVVV TGDEEEGGCC DSCGSCDRRA PDLARCECRD VVTSCGPGCK RCEEADLDLN PPRYVCKDMS FHSCQTRCSI L SEQ ID NO: 025 |
| Barley chymotrypsin inhibitor 2 | Chymotrypsin | MSSMEKKPEGVNIGAGDRQNQKTEWPELVGKSVEEAKK VILQDK PAAQIIVLPVGTIVTMEYRIDRVRLFVDRLDNIAQVPRVG SEQ ID NO: 026 |
| Thrombin inhibitors | Thrombin | IQPR SEQ ID NO: 027<br>GSAVPR SEQ ID NO: 028<br>Feng et al., (WO 2004/076484) PEPTIDE INHIBITORS OF THROMBIN AS POTENT ANTICOAGULANTS) |
| Proteosome inhibitors Chymostatin Clasto-tactastatin | Proteosome subunit 3 'chymotryptic-like' (beta5), 'tryptic-like' (beta2) and 'peptidyl-glutamyl peptide hydrolyzing' (beta1). | |
| Urokinase, thrombin, plasmin and trypsin inhibitors | Urokinase, thrombin, plasmin and trypsin | Markowska et al., 2008, Effect of tripeptides on the amindolytic activities of urokinase, thrombin, plasmin and trypsin. Int. J. Peptide Research and Therapeutics 14: 215-218. |

Therapeutic Proteins

Leader et al., 2008 (Nature Reviews Drug Discovery 7: 21-39, incorporated by reference in its entirety) divided protein therapeutics in to functional categories:

Group I: protein therapeutics with enzymatic or regulatory activity
  Ia: Replacing a protein that is deficient or abnormal.
  Ib: Augmenting an existing pathway.
  Ic: Providing a novel function or activity.
Group II: protein therapeutics with special targeting activity
  IIa: Interfering with a molecule or organism.
  IIb: Delivering other compounds or proteins.
Group III: protein vaccines
  IIIa: Protecting against a deleterious foreign agent.
  IIIb: Treating an autoimmune disease.
  IIIc: Treating cancer.
Group IV: protein diagnostics.

Although other protein therapeutics previously dominated and have had well-established production protocols (e.g., Smales, C M and James, D. C (eds) 2005, Therapeutic Proteins: Methods and Protocols, Human Press), antibody therapeutics have been the most actively developed over the past 10 years. Antibody production is well known to those skilled in the arts (e.g., Dimitrov, A. S. 2009, Therapeutic antibodies: Methods and protocols, Humana Press; Dubel, S, (ed) 2010 Handbook of therapeutic antibodies: technologies, emerging developments and approved therapeutics, Wiley-Blackwell).

Co-Administration

The protease inhibitors may be mixtures with the therapeutics, and be ionically coupled, or uncoupled to the therapeutic. Methods of preparing such mixtures are known to those skilled in the arts (Singh, M., (ed) 2007, Vaccine adjuvants and delivery systems, Wiley.

Bioconjugated Protease Inhibitors

In a preferred embodiment, the inhibitor is covalently coupled to the therapeutic. Methods of covalently linking to therapeutic proteins are known to those skilled in the arts (e.g., Bioconjugate techniques, 2nd Ed. Greg T Hermanson Academic Press, Amsterdam, 2008; Bioconjugation Protocols; Strategies and Methods. Christof M. Niemeyer, (ed), Methods in Molecular Biology 283. Humana Press, Totowa, N.J., 2010;

Genetic Fusions

In the production of therapeutic proteins, genetic constructs can be used to generate fusion proteins. The fusion proteins are generally produced as N-terminal or C-terminal fusions by the addition of DNA, in-frame, that codes for the fusion peptide. For example, the genes encoding monoclonal antibodies can be genetically engineered to be produced as peptide fusions, where the peptides are protease inhibitor peptides. The protease inhibitor peptides can be monomeric or polymeric, and may be activated through cleavage by the protease they inhibit or by other proteases. Methods of generating antibody protein fusions are well known to those skilled in the arts (e.g., Chamow, S. M and Ashkenazi, A. (eds) Antibody Fustion Proteins Wiley-Liss, New York; Kontermann, R. and Dubel, S. Antibody Engineering, Second Edition, 2010., Springer Verlag, Berlin; kreitman and Pastan, Making).

Example

A cancer therapeutic antibody coupled to a polymeric protease activated protease inhibitor.

FIG. 1 shows a polymeric protease activated protease inhibitor. Multiple protease inhibitor peptides may be used in-frame with multiple protease cleavage signals (polymeric protease activated protease inhibitors), where the inhibitors alternate with cleavage sites. The polymeric protease activated protease inhibitors can be homo- or hetero-inhibitor polymers (i.e., have multiple inhibitors for the same or different proteases, respectively), and/or homo- or heteroprotease cleavage polymers (i.e., have multiple of the same or different protease cleavage sites). Thus, protease inhibitors 1, 2 and 3 can be the same protease inhibitor or different protease inhibitors, and the protease cleavage sites (downward arrows) can be the same protease cleavage side or different protease cleavage sites.

Figure 2:
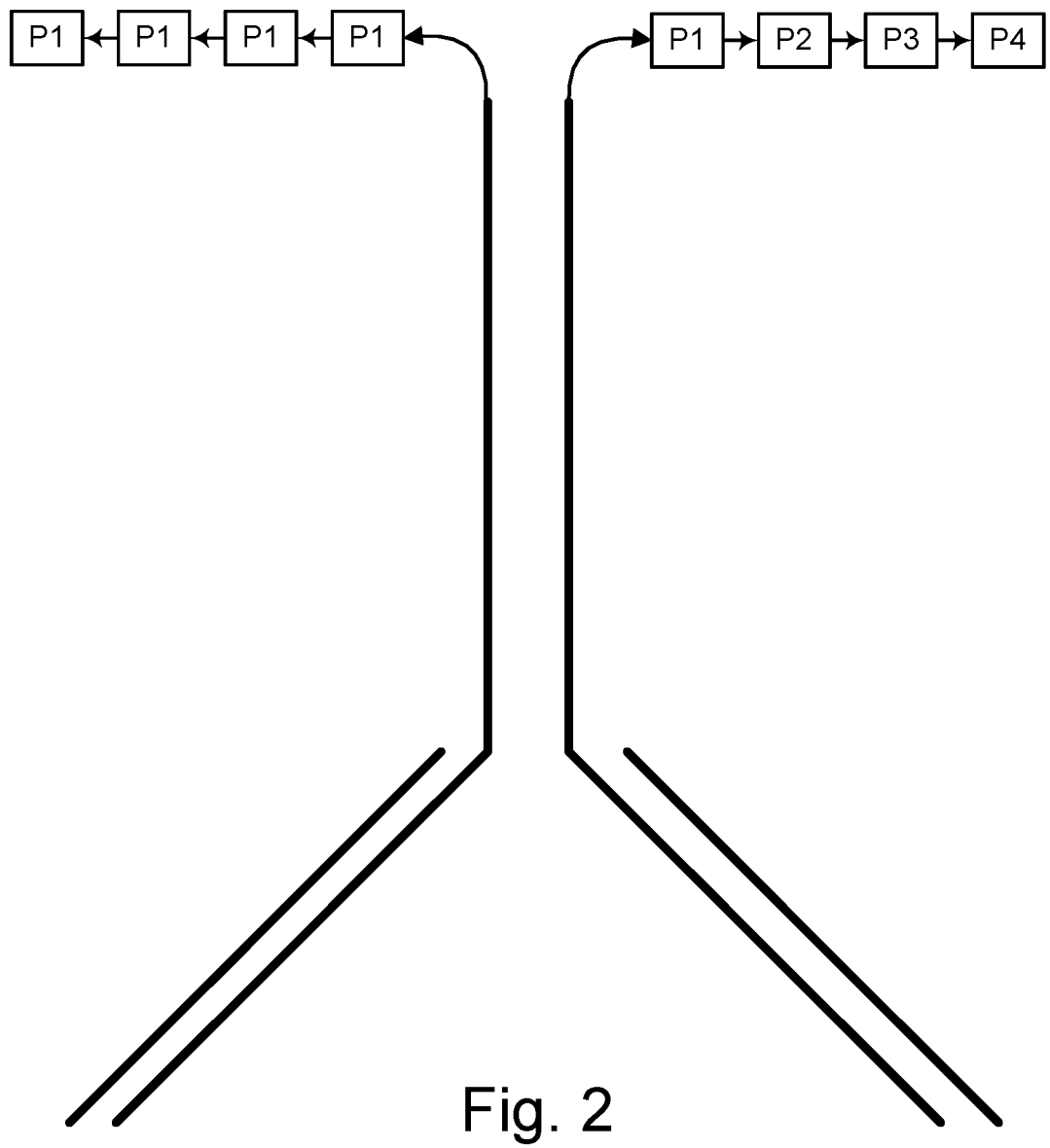
FIG. 2 shows chimeric antibody coupled to polymeric protease-activated protease inhibitors.

The protease inhibitors are those known inhibitors for proteases overexpressed in tumors, such as those from Table 2. A therapeutic antibody, such as Herceptin, is coupled to a polymeric protease-activated protease inhibitor. The polymeric protease inhibitor, such as a furin-activated furin inhibitor, in frame with the Herceptin antibody with the amino acid sequence (furin inhibitor IN CAPS; furin cleavage in lower case) TKKVAKRPRAKRAArxkr↓sxTKKVAKRPRAKRAArxkr↓sxTKKVAKRPRAKRAA, SEQ ID NO: 029, is genetically fused or covalently bound using methods known to those skilled in the arts (e.g., Bioconjugate techniques, 2nd Ed. Greg T Hermanson, Academic Press, Amsterdam, 2008; Bioconjugation Protocols; Strategies and Methods. Christof M. Niemeyer, (ed), Methods in Molecular Biology 283. Humana Press, Totowa, N.J., 2010; Chamow, S. M and Ashkenazi, A. (eds) Antibody Fusion Proteins Wiley-Liss, New York; Kontermann, R. and Dubel, S. Antibody Engineering, Second Edition, 2010, Springer Verlag, Berlin) to result in an antibody with a polymeric protease inhibitor as shown (FIG. 2). The purified conjugate is then used for the treatment of cancer by injection of an effective amount. Animal models (Teicher, B. ed.) Tumor models in Cancer Research, Humana Press, 2002) may be used to guide human clinical evaluation where dose escalation is used, often beginning with low doses calculated from animal studies.

FIG. 2 shows an antibody (IgG type) conjugated with a polymeric protease activated protease inhibitor. On the left, a homopolymer of protease inhibitor is shown. On the right, a heteropolymer of protease inhibitor is shown. The antibody may be monoclonal or polyclonal, and may act as a targeting therapeutic, catalytic antibody, or diagnostic agent.

What is claimed is:

1. A method, comprising:
   administering a protease-activated polymeric peptide protease inhibitor comprising a protease-sensitive therapeutic agent linked through a protease cleavage site to a plurality of polypeptide protease inhibitors alternating with a plurality of protease cleavage sites in sequence to an organism;
   activating a protease inhibitory activity of a peptide sequence of the protease-activated polymeric peptide protease inhibitor with a first organism protease; and
   inhibiting a second organism protease with the protease inhibitory activity of the peptide sequence of the protease-activated polymeric peptide protease inhibitor.

2. The method according to claim 1, wherein the first organism protease is of the same type of protease as the second organism protease.

3. The method according to claim 1, wherein the first organism protease is of a different type of protease than the second organism protease.

4. The method according to claim 1, wherein the protease-activated polymeric peptide protease inhibitor comprises a homopolymer of identical peptide protease inhibitors.

5. The method according to claim 1, wherein the protease-activated polymeric peptide protease inhibitor comprises a heteropolymer of different peptide protease inhibitors.

6. The method according to claim 1, wherein the first organism protease cleaves the protease cleavage site which binds the protease-sensitive therapeutic agent to the plurality of polypeptide protease inhibitors alternating with a plurality of protease cleavage sites in sequence.

7. The method according to claim 1, wherein the protease-sensitive therapeutic agent is a protease-sensitive antibody.

8. The method according to claim 1, wherein the protease-activated polymeric peptide protease inhibitor comprises a plurality of identical polypeptide protease inhibitors, wherein the protease-activated polymeric peptide protease inhibitor is purified.

9. The method according to claim 8, wherein the plurality of protease cleavage sites are subject to cleavage by the second organism protease.

10. The method according to claim 8, wherein at least one protease cleavage site is subject to cleavage by a different protease from the second organism protease.

11. The method according to claim 1, wherein the plurality of polypeptide protease inhibitors comprise a plurality of different types of polypeptide protease inhibitors, wherein the protease-activated polymeric peptide protease inhibitor is purified.

12. The method according to claim 11, wherein the plurality of protease cleavage sites comprise a plurality of different protease cleavage sites which are respectively cleaved by a plurality of different organism proteases, subject to inhibition by the plurality of different types of polypeptide protease inhibitors.

13. The method according to claim 11, wherein the plurality of protease cleavage sites comprise a protease cleavage site cleavable by at least one protease which is not inhibited by the plurality of different types of polypeptide protease inhibitors.

14. The method according to claim 11, wherein the plurality of different polypeptide protease inhibitors are configured to inhibit a plurality of different classes of proteases.

15. The method according to claim 1, wherein the protease-sensitive therapeutic agent protease comprises a cleavage site cleavable by the second organism protease, whereby degradation of the protease-sensitive therapeutic agent by the second organism protease is delayed.

16. The method according to claim 1, wherein the protease-sensitive therapeutic agent has at least one furin cleavage site wherein cleavage of the furin cleavage site of the protease-sensitive therapeutic agent leads to inactivation of the protease-sensitive therapeutic agent, and the plurality of polypeptide protease inhibitors in sequence comprise a plurality of furin inhibitor peptide sequences linked through respective furin cleavage sites.

17. A method, comprising:
    administering to an organism a polypeptide, comprising a protease-activated polymeric peptide protease inhibitor having a plurality of protease inhibitor domains which, after activation, inhibit a protease of the organism, separated by a plurality of protease cleavage sites cleavable by the protease of the organism, in conjunction with a protease-sensitive agent degradable by the protease of the organism;
    cleaving the plurality of protease cleavage sites with the protease of the organism, to thereby activate the protease inhibitor domains; and
    inhibiting the protease of the organism with the activated protease inhibitor domains, to thereby inhibit degradation of the protease-sensitive agent.

18. A method, comprising:
    administering an inactive protease-activated polymeric peptide protease inhibitor to an organism in conjunction with a protease-sensitive therapeutic agent for treating a neoplastic disease of the organism, the protease-sensitive therapeutic agent being subject to proteolytic degradation by the organism, to thereby treat the neoplastic disease;
    activating the inactive protease-activated polymeric peptide protease inhibitor with at least one protease in the organism to cleave at least one protease cleavage site to produce at least one active protease inhibitor domain from the inactive protease-activated polymeric peptide protease inhibitor; and
    inhibiting the proteolytic degradation by the organism of the protease-sensitive therapeutic agent, with the at least one active protease inhibitor domain.

* * * * *